(12) United States Patent
Bryant et al.

(10) Patent No.: US 11,402,361 B2
(45) Date of Patent: Aug. 2, 2022

(54) PERSONNEL-TOLERANT CARBON DIOXIDE BEAMLINE VARIATION REDUCTION

(71) Applicant: International Business Machines Corporation, Armonk, NY (US)

(72) Inventors: Shane D. Bryant, Albany, NY (US); Robert Young, Poestenkill, NY (US); Christopher F. Robinson, Hyde Park, NY (US); Kelly Bronson, Glenmont, NY (US)

(73) Assignee: International Business Machines Corporation, Armonk, NY (US)

( * ) Notice: Subject to any disclaimer, the term of this patent is extended or adjusted under 35 U.S.C. 154(b) by 670 days.

(21) Appl. No.: 16/436,420

(22) Filed: Jun. 10, 2019

(65) Prior Publication Data
US 2020/0386729 A1    Dec. 10, 2020

(51) Int. Cl.
*H01J 37/32*    (2006.01)
*H01J 37/317*   (2006.01)
*G01N 33/00*    (2006.01)

(52) U.S. Cl.
CPC ....... *G01N 33/004* (2013.01); *G01N 33/0031* (2013.01); *H01J 37/3174* (2013.01); *H01J 37/32449* (2013.01); *H01J 2237/006* (2013.01)

(58) Field of Classification Search
CPC .................. H01J 37/32449; H01J 37/3174
See application file for complete search history.

(56) References Cited

U.S. PATENT DOCUMENTS

| | | |
|---|---|---|
| 6,579,344 B1 | 6/2003 | Diserens |
| 8,449,806 B2 | 5/2013 | Miyairi et al. |
| 9,269,528 B2 | 2/2016 | Kaim et al. |
| 2008/0219317 A1 | 9/2008 | Pettit et al. |
| 2017/0030942 A1 | 2/2017 | Anderson |

FOREIGN PATENT DOCUMENTS

| | | |
|---|---|---|
| CN | 102476244 A | 5/2012 |
| CN | 204330540 U | 5/2015 |
| JP | 2011185567 A | 9/2011 |
| JP | 2013228296 A | 11/2013 |
| JP | 2017131904 A | 8/2017 |

OTHER PUBLICATIONS

Commercial Micro Manufacturing International, Laser Technologies for Semiconductor Manufacturing: A Massive Adoption, www.cmmmagazine.com/micromanufacturing/lasers/laser-technologies-for-semiconductor-manufacturing-a-massive/, Oct. 17, 2017, 3 pages.

*Primary Examiner* — Joseph L Williams
(74) *Attorney, Agent, or Firm* — Abdy Raissinia; Ryan, Mason & Lewis, LLP (57) ABSTRACT

A method of controlling a gas mixture for a laser includes receiving as an input one or more of a plurality of concentration values. Each of the concentration values respectively corresponds to a constituent of a plurality of constituents of air. In the method, a blend of the plurality of constituents of air is generated based on the received one or more of the concentration values. The method also includes determining whether the blend of the plurality of constituents of air is within a threshold range for a ratio of the concentration values for the plurality of constituents of air. A flow of the blend of the plurality of constituents of air is controlled to be routed through an output circuit for use as the gas mixture for the laser following a determination that the blend of the plurality of constituents of air is within the threshold range.

20 Claims, 7 Drawing Sheets

PERSONNEL-TOLERANT CARBON DIOXIDE BEAMLINE VARIATION REDUCTION

BACKGROUND

Periodic fluctuations of the concentration of carbon dioxide ($CO_2$) in air occur naturally in the atmosphere, and $CO_2$ concentration fluctuations in a laser beam path result in fluctuations in drive laser beam diameter. A drive laser can be used in a laser produced plasma source to vaporize tin droplets generating extreme ultraviolet (EUV) radiation from the tin plasma. The fluctuations in drive laser beam diameter cause corresponding fluctuations in energy per pulse of EUV scanner radiation, which may be used, for example, in semiconductor lithography processes. Laser beam diameter fluctuations during semiconductor processing further result in degraded tin droplet targeting and EUV dose errors during periods of high $CO_2$ content, contribute to rapid collector contamination, and lead to increased EUV scanner maintenance requirements.

Industrial compressed dry air (CDA) is often required by semiconductor processing equipment. The known industrial or fabrication facility site (fab-site) CDA production processes do not specifically control $CO_2$ concentrations, and the drying process can even exacerbate fluctuations that perturb the laser beam diameter. In different laser systems, such fluctuations may include "dips" and "oscillations." Dips are sudden drops in laser beam size, which exhibit slow recovery to the larger beam size and longer periods of the larger beam diameter than the smaller beam diameter. Oscillations refer to slow and systematic variations of laser beam diameter.

Accordingly, there is a need for systems and techniques for limiting laser beam $CO_2$ variations in order to prevent unwanted fluctuations in laser beam size.

SUMMARY

According to an exemplary embodiment of the present invention, a method of controlling a gas mixture for a laser includes receiving as an input one or more of a plurality of concentration values. Each of the plurality of concentration values respectively corresponds to a constituent of a plurality of constituents of air. In the method, a blend of the plurality of constituents of air is generated based on the received one or more of the plurality of concentration values. The method also includes determining whether the blend of the plurality of constituents of air is within a threshold range for a ratio of the plurality of concentration values for the plurality of constituents of air. A flow of the blend of the plurality of constituents of air is controlled to be routed through an output circuit for use as the gas mixture for the laser following a determination that the blend of the plurality of constituents of air is within the threshold range.

According to an exemplary embodiment of the present invention, a system for controlling a gas mixture for a laser includes a memory and at least one processor coupled to the memory, wherein the at least one processor is configured to receive as an input one or more of a plurality of concentration values. Each of the plurality of concentration values respectively corresponds to a constituent of a plurality of constituents of air. The processor is further configured to generate a blend of the plurality of constituents of air based on the received one or more of the plurality of concentration values, and to determine whether the blend of the plurality of constituents of air is within a threshold range for a ratio of the plurality of concentration values for the plurality of constituents of air. The processor is also configured to control a flow of the blend of the plurality of constituents of air to be routed through an output circuit for use as the gas mixture for the laser following a determination that the blend of the plurality of constituents of air is within the threshold range.

According to an exemplary embodiment of the present invention, a computer program product for controlling a gas mixture for a laser includes a computer readable storage medium having program instructions embodied therewith, the program instructions executable by a processor to cause the processor to perform a method including receiving as an input one or more of a plurality of concentration values. Each of the plurality of concentration values respectively corresponds to a constituent of a plurality of constituents of air. In the method, a blend of the plurality of constituents of air is generated based on the received one or more of the plurality of concentration values. The program instructions further cause the processor to perform the steps of determining whether the blend of the plurality of constituents of air is within a threshold range for a ratio of the plurality of concentration values for the plurality of constituents of air, and controlling a flow of the blend of the plurality of constituents of air to be routed through an output circuit for use as the gas mixture for the laser following a determination that the blend of the plurality of constituents of air is within the threshold range.

These and other illustrative embodiments of the invention will be described in or become apparent from the following detailed description of exemplary embodiments, which is to be read in connection with the accompanying drawings.

DETAILED DESCRIPTION

Illustrative embodiments will be described below for creating a custom blend of synthetic air that is suitable as a laser sheath gas, and is a breathable mixture of gas which is safe for human consumption.

As used herein, a "laser sheath gas" or "sheath gas" refers to the gas used to purge a laser beam line. The purge gas fills the volume within the drive laser enclosure walls or "sheath". For the most part the $CO_2$ laser beam does not interact with the CDA used to purge the beam enclosure. The exception is that some $CO_2$ radiation is absorbed by the small percentage of $CO_2$ gas in the CDA. This heats up the sheath gas, thereby changing the refractive index of the $CO_2$ beam path, which results in a defocus or broadening of the $CO_2$ drive laser beam diameter.

As used herein, "constituents of air" or "air constituents" refer to elements or compounds found in the normal Earth atmosphere, including, nitrogen, oxygen, argon and $CO_2$. Concentrations of these air constituents are normally about 0.04% $CO_2$, about 0.93% argon, about 20.95% oxygen and about 78.09% nitrogen.

Figure 1:
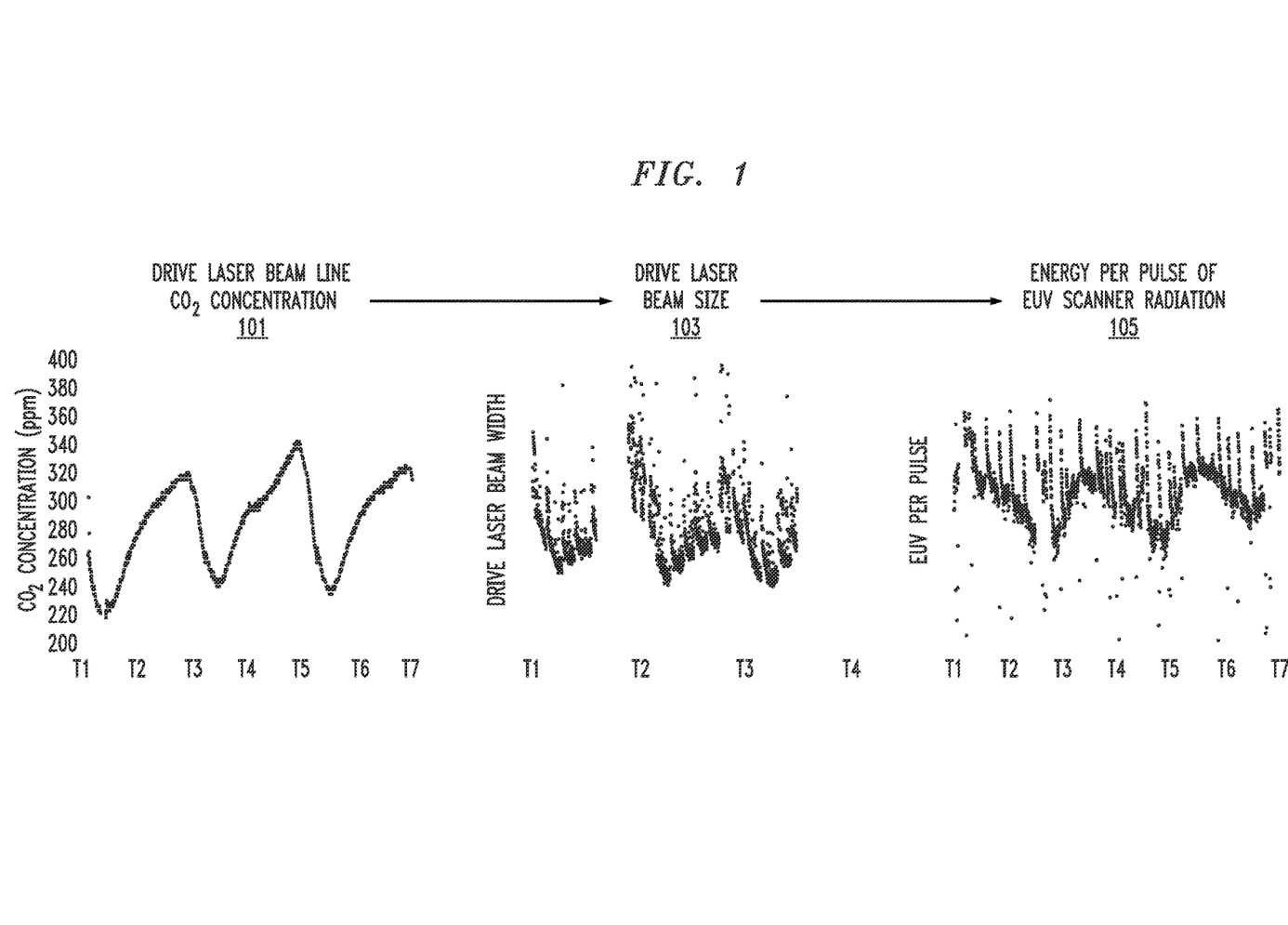
FIG. 1 illustrates graphs showing an impact of laser beam line $CO_2$ concentration fluctuations on laser beam size and laser pulse energy.

FIG. 1 illustrates graphs showing an impact of laser beam line $CO_2$ concentration fluctuations on laser beam size and laser pulse energy. For example, graph 101 shows fluctuations in laser beam line $CO_2$ concentration (ppm) over a plurality of times T1, T2, T3, T4, T5, T6 and T7. For example, an interval between each time T in graph 101 may be 12 hours, but the embodiments are not limited thereto. Graph 103 illustrates resulting changes in drive laser beam width over a plurality of times T1, T2, T3 and T4 corresponding to the fluctuations in laser beam line $CO_2$ concentration in graph 101. The vertical axis of graph 103 represents the beam diameter in microns (μm). The graph 103 shows the size variation over time, which correlates with the other graphs (101 and 105) of $CO_2$ concentration variation in delivered air and pulse energy variation. An interval between each time T in graph 103 may be 24 hours, but the embodiments are not limited thereto. Graph 105 illustrates resulting changes in energy per pulse of EUV scanner radiation (mJ) over a plurality of times T1, T2, T3, T4, T5, T6 and T7 corresponding to the fluctuations in drive laser beam line $CO_2$ concentration in graph 101, and fluctuations in drive laser beam width in graph 103. An interval between each time T in graph 105 may be 12 hours, but the embodiments are not limited thereto. As can be understood from graphs 101, 103 and 105, scanner EUV energy instability tracks cyclic variations in drive laser beam line $CO_2$ concentration.

In one or more embodiments, drive laser beam line variation is reduced by tuning mixing ratios of synthetic purified gases to control and potentially alter the natural air ratios of about 0.04% $CO_2$, about 0.93% argon, about 20.95% oxygen and about 78.09% nitrogen. The tuning is performed using precision components, such as, for example, precision flow controllers (PFCs) suitable for semiconductor fabrication applications. The embodiments also provide downstream verification and air constituent concentration monitoring using controlled loop feedback to maintain precise control of the atmospheric constituents of $CO_2$, argon, oxygen and nitrogen.

The embodiments advantageously control amounts of parasitic molecules in the beam path, eliminate hazardous breathing environments and enable stable laser beam diameter control. For example, the embodiments create a custom blend of synthetic air (e.g., CDA) that limits or prevents $CO_2$ variations, is usable as a laser sheath gas, and is a breathable mixture of gases safe for human consumption.

Illustrative embodiments provide methods and systems which enable precise concentration control of one or more atmospheric constituents in order to optimize overall laser beam performance, control and repeatability. Advantageously, illustrative embodiments provide for direct user control of gas ratios, providing users with implementation flexibility and ability to tune laser beam diameter at their discretion. Moreover, as an advantage over current technology, the embodiments eliminate external variables and potential introduction of contaminants as has been observed with conventional $CO_2$ removal and purification techniques or treatment cycles.

Figure 2:
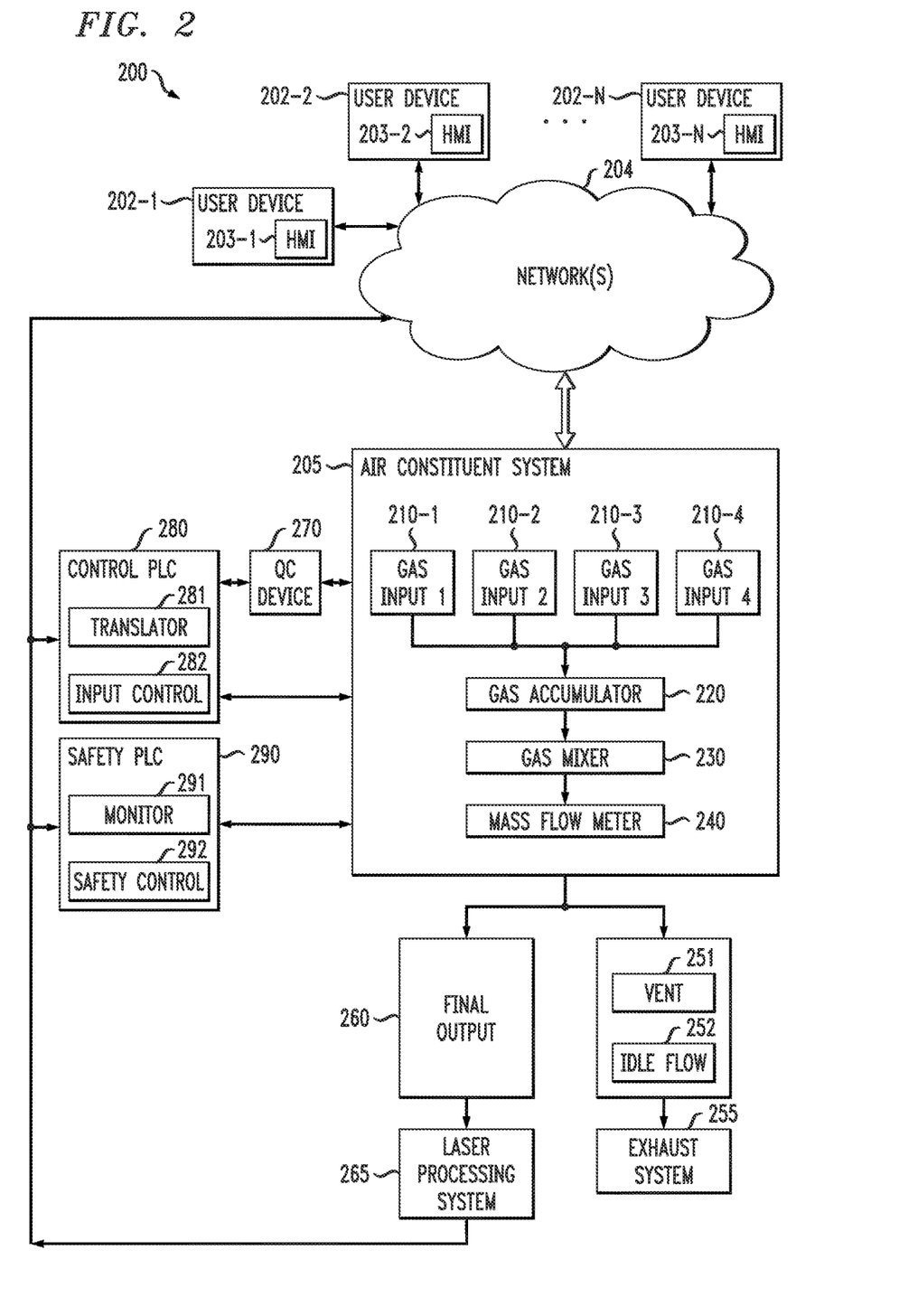
FIG. 2 is a block diagram of a synthetic air blending system including an air constituent system, according to one or more embodiments of the invention.

FIG. 2 is a block diagram of a synthetic air blending system 200 including an air constituent system 205, according to one or more embodiments of the invention. As shown in FIG. 2 by lines and/or arrows, the components of the system 200 are operatively connected to each other via, for example, physical connections, such as gas tubing, wired and/or direct electrical contact connections, and/or wireless connections, such as, for example, WiFi, BLUETOOTH, IEEE 802.11, and/or networks, including but not limited to, a local area network (LAN), wide area network (WAN), cellular network, ad hoc networks, WANET, satellite network or the Internet. For example, a network 204 can operatively link one or more components 202-1, 202-2, ..., 202-N, 205, 280, 290 and 265 of the system 200.

By way of non-limiting example, in accordance with an embodiment of the present invention, referring to FIG. 2, the system 200 includes user devices 202-1, 202-2, ... 202-N (collectively "user devices 202). The variable N is an integer greater than one. The user devices 202 communicate over the network 204 with, for example, air constituent system 205, control programmable logic controller (PLC) 280, safety PLC 290 and/or laser processing system 265.

The user devices 202 can comprise, for example, desktop, laptop or tablet computers, mobile telephones, or other types of processing devices capable of communicating with, for example, air constituent system 205, control PLC 280, safety PLC 290 and/or laser processing system 265 over the network 204. Outputs from the air constituent system 205, control PLC 280, safety PLC 290 and/or laser processing system 265 including, for example, operational details regarding the concentration values of gases (e.g., air constituents such as nitrogen, oxygen, argon and $CO_2$) in a laser gas mixture, whether the gas mixture is safe for human consumption, laser beam size, operational pressures and/or volumetric flow, are communicated to the user devices 202 via, for example, network(s) 204.

The system 200 includes a number of components to create a synthetic blend of the four largest species of gas (nitrogen, oxygen, argon and $CO_2$) that make up 99.998% of the air that is in the Earth's atmosphere. The system 200 utilizes a control PLC 280 and a safety PLC 290 to create a custom blend of gas based on a safe parameter set of inputs for the concentrations of air constituents of nitrogen, oxygen, argon and $CO_2$ in the custom gas blend. The four inputs of the air constituent system 205 (gas input 1 210-1, gas input 2 210-2, gas input 3 210-3 and gas input 4 210-4) respectively correspond to a nitrogen input, oxygen input, argon input and $CO_2$ input. Each of the four inputs 210-1, 210-2, 210-3 and 210-4 is assigned an acceptable concentration range that yields a normal breathable balance of the constituents that would be safe for human consumption. For example, in a non-limiting embodiment, an acceptable concentration range tolerance for yielding safe and breathable air is predefined in the system as ±0.04% for concentration values of 0.04% $CO_2$, 0.93% argon, 20.95% oxygen and 78.09% nitrogen. The embodiments are not necessarily limited to the noted tolerance or concentration values, and variations may be made based on what is known to be safe ratios of the noted four constituents of air to create a mixture that is safe for human consumption.

The embodiments permit maintenance of a safe breathable gas mixture to be generated for use in a laser processing system 265, while allowing for custom tailoring of the final blend of constituents to control a size of the resulting drive laser beam and optimize the resultant EUV photon energy and delivery from a source to a sink. According to an embodiment, command and active feedback is utilized so that the blend of gas is vented to an exhaust system 255 until the blend is determined by the safety PLC 290 to be in the safe breathable range as defined by the acceptable concentration range tolerance for concentration values of nitrogen, oxygen, argon and $CO_2$. Following a determination that the blend of the plurality of constituents of air is within the threshold range for concentration values of nitrogen, oxygen, argon and $CO_2$, the flow of the gas mixture can be controlled so that the gas mixture is transferred from vent/idle flow circuits 251, 252 to a final output circuit 260 to be transmitted to the laser processing system 265 for use as a laser sheath gas.

Figure 3:
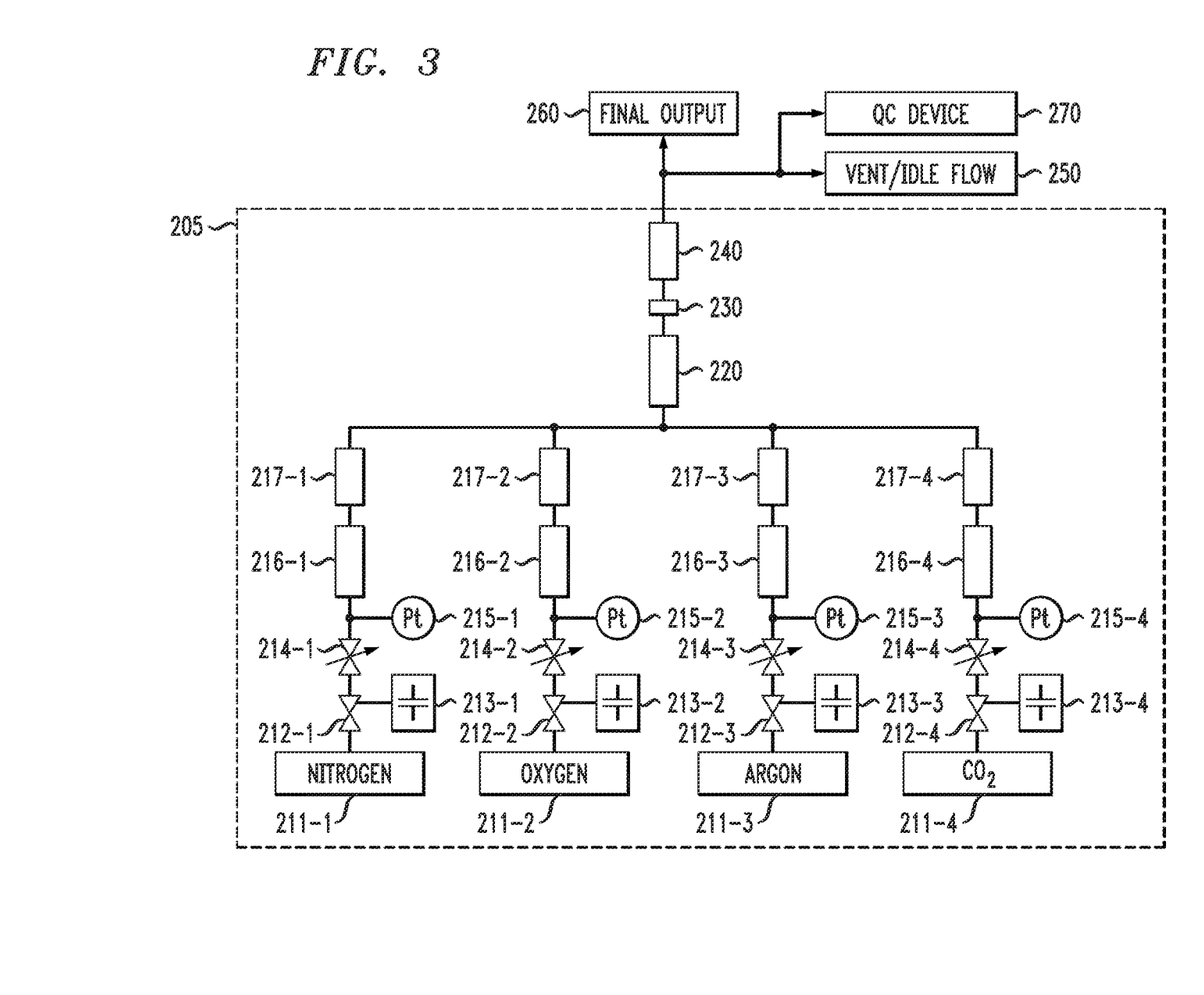
FIG. 3 is a block diagram of the air constituent system described in connection with FIG. 2, according to one or more embodiments of the invention.

Referring to FIG. 3, each of the gas inputs 210-1 to 210-4 includes a plurality of components which are implemented at the individual air constituent level to create the blend of gases resulting in a safe breathable gas mixture and customized final blend of constituents to produce a gas mixture which results in a desired drive laser beam size (e.g., diameter/width) with optimized EUV pulse energy. According to an embodiment, each of the gas inputs 210-1 to 210-4 includes a gas inlet 211-1, 211-2, 211-3 and 211-4 through which the constituent gas (nitrogen, oxygen, argon or $CO_2$) is supplied. The individual constituent gases flow from the gas inlets 211-1, 211-2, 211-3 and 211-4 to respective inlet valves 212-1, 212-2, 212-3 and 212-4, which are normally closed valves that are opened to permit gas to flow through the valves 212-1 to 212-4.

The inlet valves 212-1, 212-2, 212-3 and 212-4 are operatively coupled to respective inlet valve end switches 213-1, 213-2, 213-3 and 213-4 which are used to control opening and closing of the valves 212-1 to 212-4. The status of the inlet valve end switches 213-1 to 213-4, indicating whether the vales 212-1 to 212-4 are open or closed, is provided to the safety PLC 290 to ensure safe operation, and to the control PLC 280 for functional control of the gas inputs 210-1 to 210-4.

The inlet valves 212-1, 212-2, 212-3 and 212-4 are operatively coupled to respective regulators 214-1, 214-2, 214-3 and 214-4, which are used to regulate the corresponding constituent gas to the proper operational pressure. Pressure transducers 215-1, 215-2, 215-3 and 215-4 positioned after the outputs of the respective regulators 214-1, 214-2, 214-3 and 214-4 measure the pressure of the corresponding constituent gas. According to an embodiment, the gas flow pressures after the outputs of the regulators 214-1 to 214-4 are converted into analog electrical signals of 4-20 mA by the pressure transducers 215-1 to 215-4, and the signals are transmitted to the safety PLC 290 and the control PLC 280. The safety and control PLCs 290 and 280 are programmed to convert the mA signals to pressure values. PLCs 280 and 290 ensure all relative pressures are equal so that no single gas can dominate the others and affect the mix ratio.

Following output from the regulators 214-1 to 214-4, the constituent gases of the gas inputs 210-1 to 210-4 flow through respective constituent mass flow controllers (MFCs) 216-1, 216-2, 216-3 and 216-4. Each MFC 216-1 to 216-4 is a precision flow controller which functions based on a control setpoint to set the constituent gas flow to output the corresponding constituent gas at a particular flow rate which will result in a desired concentration value of the constituent gas. The resulting concentration value yields a breathable mixture of air and a desired size of the laser beam. The MFCs 216-1, 216-2, 216-3 and 216-4 receive and transmit data from and to the control PLC 280. The input control component 282 of the control PLC 280 controls the MFC setpoints and generates setting adjustments based on user input regarding the concentration values and/or feedback regarding measured flow rates.

Following output from the MFCs 216-1 to 216-4, the constituent gases of the gas inputs 210-1 to 210-4 flow through respective mass flow meters (MFMs) 217-1, 217-2, 217-3 and 217-4. Each MFM 217-1 to 217-4 is a precision meter for measuring volumetric flow of each constituent gas. The measured volumetric flow is provided to the safety PLC 290 and/or the control PLC 280. According to one or more embodiments, a monitor component 291 of the safety PLC 290 includes programmable logic to analyze measured volumetric flow and determine whether the measured volumetric flow translates to a desired concentration value of the constituent gas yielding a breathable mixture of air. According to an embodiment, if the safety PLC 290 (e.g., monitor component 291) determines that the measured volumetric flow of one or more of the constituents does not translate to a desired concentration value of the constituent gas yielding a breathable mixture of air, the safety control component 292 of the safety PLC 290 sends a message to the control PLC 280 indicating that one or more of the constituent gases has a concentration which is out of a safe range. The input control component 282 of the control PLC 280 sends a command to one or more of the MFCs 216-1 to 216-4 to adjust the flow of their corresponding constituents of air in order to achieve the desired concentration value of the constituent gas yielding a breathable mixture of air.

According to one or more embodiments, the control PLC 280 includes programmable logic to analyze measured volumetric flow and determine whether the measured volumetric flow translates to a desired concentration value of the constituent gas yielding a desired size of the laser beam. According to an embodiment, if the control PLC 280 determines that the measured volumetric flow of one or more of the constituents does not translate to a desired concentration value of the constituent gas yielding a desired size of the laser beam, the input control component 282 of the control PLC 280 sends a command to one or more of the MFCs 216-1 to 216-4 to adjust the flow of their corresponding constituents of air in order to achieve the desired concentration value of the constituent gas yielding a desired size of the laser beam.

The air constituent system 205 includes a gas accumulator 220 where the constituents of the gas mixture from gas input 1 210-1, gas input 2 210-2, gas input 3 210-3 and gas input 4 210-4 (nitrogen, oxygen, argon and $CO_2$) converge. According to an embodiment, minute differences in the input pressures of the individual gases normalize and a first stage of gas mixing occurs in the gas accumulator 220.

The gas mixture from the gas accumulator 220 flows to the gas mixer 230. The gas mixer 230 is a mechanical device that causes gas molecules of different sizes and masses to mix and collide without creating flow restrictions or changes in conductance that would limit the molecular flow of the gas mixture through the air constituent system 205.

The air constituent system 205 includes a mass flow meter 240 operatively coupled to the gas mixer 230 to receive an output gas flow from the gas mixer 230. The mass flow meter 240 is a precision flow meter measuring volumetric flow of the blend of the constituents of air.

A value for the volumetric flow of the blend of the constituents of air obtained from the mass flow meter 240 can be used to ensure by comparison that total gas flow demand is met. Values for the volumetric flow of the blend of the constituents of air obtained from the quality control device 270 can also be used to determine whether the blend of the constituents of air conforms to desired concentration values of one or more of the air constituents (e.g., $CO_2$ concentration value) set, for example, by the system 200 or a user, to result in a specific size of the drive laser beam that determines an associated energy of EUV pulses generated by impingement of the drive laser on provided tin droplets. Fixing the $CO_2$ content of the drive laser purge gas stabilizes the purge gas temperature and refractive index, resulting in more stable drive laser beam width and ultimately more consistent generation of EUV radiation.

According to an embodiment, the mass flow meter 240 is used as a relative device, and is not gas specific but can be set to the most desirable setting for the individual user. Ideally the gas correction factor would be set for normal atmospheric air. Mass flow meter 240 is a single point monitor of the delivered total blended gas flow for the purpose of comparing with user demand flow.

According to an embodiment, the mass flow meter 240 is used by the control PLC 280 to create a single control signal outlet. Mass flow meter 240 is a final check of the aggregate of all system constituents to display the total system output flow.

The safety PLC 290 includes the monitor component 291 to monitor and control specific hardware of the system 200 in order to maintain the laser gas as a safe breathable air mixture. For example, the safety PLC 290 receives input from a variety of devices including, but not necessarily limited to, pressure transducers 215-1, 215-2, 215-3 and 215-4, MFMs 217-1 to 217-4, MFM 240 and/or quality control device 270. If a safety issue is determined by the safety PLC 290, the safety control component 292 sends a message to the control PLC 280 with data regarding the cause of the safety issue (e.g., unsafe concentration of one or more of the constituents of air) so that control PLC 280 (e.g., input control component 282) can issue a command to the appropriate hardware (e.g., MFC 216-1 to 216-4) to address the issue. Alternatively, the safety PLC 290 may be programmed to send a command directly to the appropriate hardware (e.g., MFC 216-1 to 216-4) to address the issue.

For example, in the event that the safety PLC 290 determines an unsafe ratio of the individual constituents of air, the system 200 can control flow of the blend of constituents by opening a valve to a vent circuit 251 leading to an exhaust system 255, and closing a valve to a final output circuit 260 leading to a laser processing system 265. The control of the flow may be performed through the safety control component 292 of the safety PLC 290 and the input control component 282 of the control PLC 280, or directly from the safety control component 292 of the safety PLC 290.

The embodiments include an idle vent circuit 252, which is used if the process is out cycled through periods of static and dynamic control. The idle vent circuit 252 maintains a safe flow of a total or reduced flow of the gas mixture. Employing the idle vent circuit 252 maintains a complete mix of the gas species for immediate transfer to the laser processing system 265 for optimal use. Idle vent 252 is used to minimize variations in the blended gas ratios when switching from idle to final output 260.

According to an embodiment, in an effort to economize the use of the four input constituents of nitrogen, oxygen, argon and $CO_2$, the control PLC 280 could utilize a lower set of setpoints for each of the four MFCs 216-1 to 216-4. Control PLC 280 switching between modes of operation (final output and vent/idle flow) changes the demand to each mass flow controller whereby vent/idle flow demands a small fraction of flow versus final output flow. Specific values are determined by user input.

The system 200 includes the quality control device 270, which generates a continuous output signal utilized for data logging for process control, which is reported to the control PLC 280.

Each of the user devices 202-1, 202-2, . . . 202-N includes a human machine interface (HMI) 203-1, 203-2, . . . 203-N, which is an interface between users and control system hardware, such as, for example, air constituent system 205, control and safety PLCs 280 and 290 and the elements thereof. The HMIs 203-1, 203-2, . . . 203-N provide, for example, user interfaces, such as graphical user interfaces (GUIs) where operational system controls could be viewed, operational input could be entered and normal system operation could be viewed.

The control PLC 280 includes operational code that drives the system 200 to a specific ratio of the air constituents. The control PLC 280 includes a translator 281 that translates user input(s) to drive operation of the air constituent system 205 to control the four constituent gas inputs 210-1 to 210-4, and concentrations of the corresponding air constituents. According to an embodiment, the control PLC 280 executes an algorithm to recognize safe and unsafe air constituent ratios when one or more air constituent inputs are modified. Whether the air constituent ratios are safe or unsafe may be based on programmed threshold tolerances for the gas mixture, such as, for example, ±0.04% for concentration values of 0.04% $CO_2$, 0.93% argon, 20.95% oxygen and 78.09% nitrogen.

Figure 4:
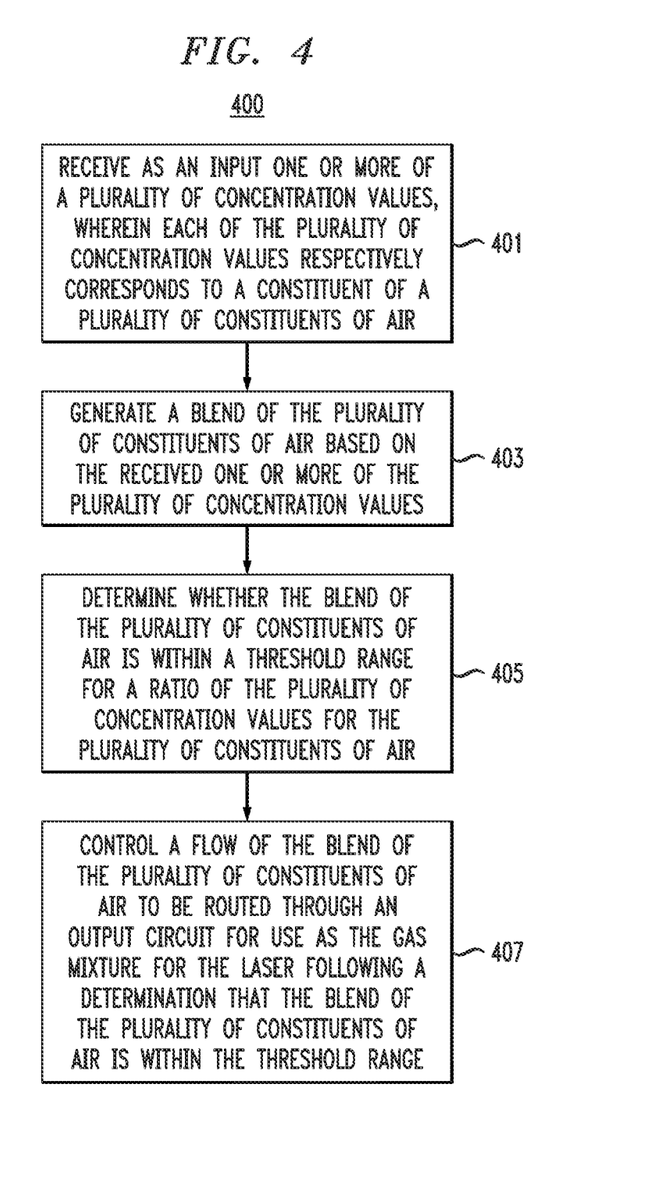
FIG. 4 illustrates a methodology for controlling an air mixture for a laser, according to one or more embodiments of the invention.

FIG. 4 illustrates a methodology for controlling an air mixture for a laser, according to one or more embodiments of the invention. Referring to FIG. 4, the methodology 400 includes, at blocks 401 and 403 respectively, receiving as an input one or more of a plurality of concentration values, and generating a blend of the plurality of constituents of air based on the received one or more of the plurality of concentration values. Each of the plurality of concentration values respectively corresponds to a constituent of a plurality of constituents of air. The plurality of constituents of air comprise nitrogen, oxygen, argon and $CO_2$.

At block 405, the methodology 400 includes determining whether the blend of the plurality of constituents of air is within a threshold range for a ratio of the plurality of concentration values for the plurality of constituents of air. The threshold range corresponds to a predetermined deviation from the ratio of the plurality of concentration values for the plurality of constituents of air, wherein the ratio is about 0.04% $CO_2$, about 0.93% argon, about 20.95% oxygen and about 78.09% nitrogen. According to an embodiment, the deviation can be, for example, ±0.04%.

At block 407, the methodology 400 further includes controlling a flow of the blend of the plurality of constituents of air to be routed through an output circuit for use as the gas mixture for the laser following a determination that the blend of the plurality of constituents of air is within the threshold range.

Prior to determining that the blend of the plurality of constituents of air is within the threshold range, a flow of the blend of the plurality of constituents of air is controlled to be routed through an exhaust system. A flow of the blend of the plurality of constituents of air can further be controlled to be transferred from a vent circuit to the output circuit following the determination that the blend of the plurality of constituents of air is within the threshold range.

According to one or more embodiments, a flow of one or more of the plurality of constituents of air through one or more precision devices is respectively monitored. For example, the flow of nitrogen, oxygen, argon and $CO_2$ through pressure transducers 215-1, 215-2, 215-3 and 215-4, and MFMs 217-1, 217-2, 217-3 and 217-4 is monitored, and feedback from the monitoring is provided to the control and/or safety PLCs 280 and 290. Determining whether the blend of the plurality of constituents of air is within the threshold range includes respectively monitoring the flow of one or more of the plurality of constituents of air through the one or more precision devices.

According to one or more embodiments, a flow of the blend of the plurality of constituents of air through one or more precision devices is monitored. For example, the flow of the blend of nitrogen, oxygen, argon and $CO_2$ through MFM 240 is monitored, and feedback from the monitoring is provided to the control and/or safety PLCs 280 and 290. Determining whether the blend of the plurality of constituents of air is within the threshold range includes monitoring the flow of the blend of the plurality of constituents of air through the one or more precision devices.

In accordance with an embodiment, a command mat be transmitted to close the output circuit 260 and to control a flow of the blend of the plurality of constituents of air to be routed through the exhaust system 255 following a determination that the blend of the plurality of constituents of air is outside of the threshold range.

According to one or more embodiments, feedback is transmitted to a user regarding the size of a drive laser beam that results when using the blend of the plurality of constituents of air as the gas mixture. Through an interface (e.g., HMI 203-1, 203-2, . . . 203-N), the user inputs a command to alter the one or more of the plurality of concentration values in response to the transmitted feedback, and an altered blend of the plurality of constituents of air is generated based on the command to alter the one or more of the plurality of concentration values. The generation of the altered blend may be performed via the control PLC 280, which is configured to control operation of one or more of the gas inputs 201-1 to 210-4, and resulting concentrations of their corresponding air constituents.

Figure 5:
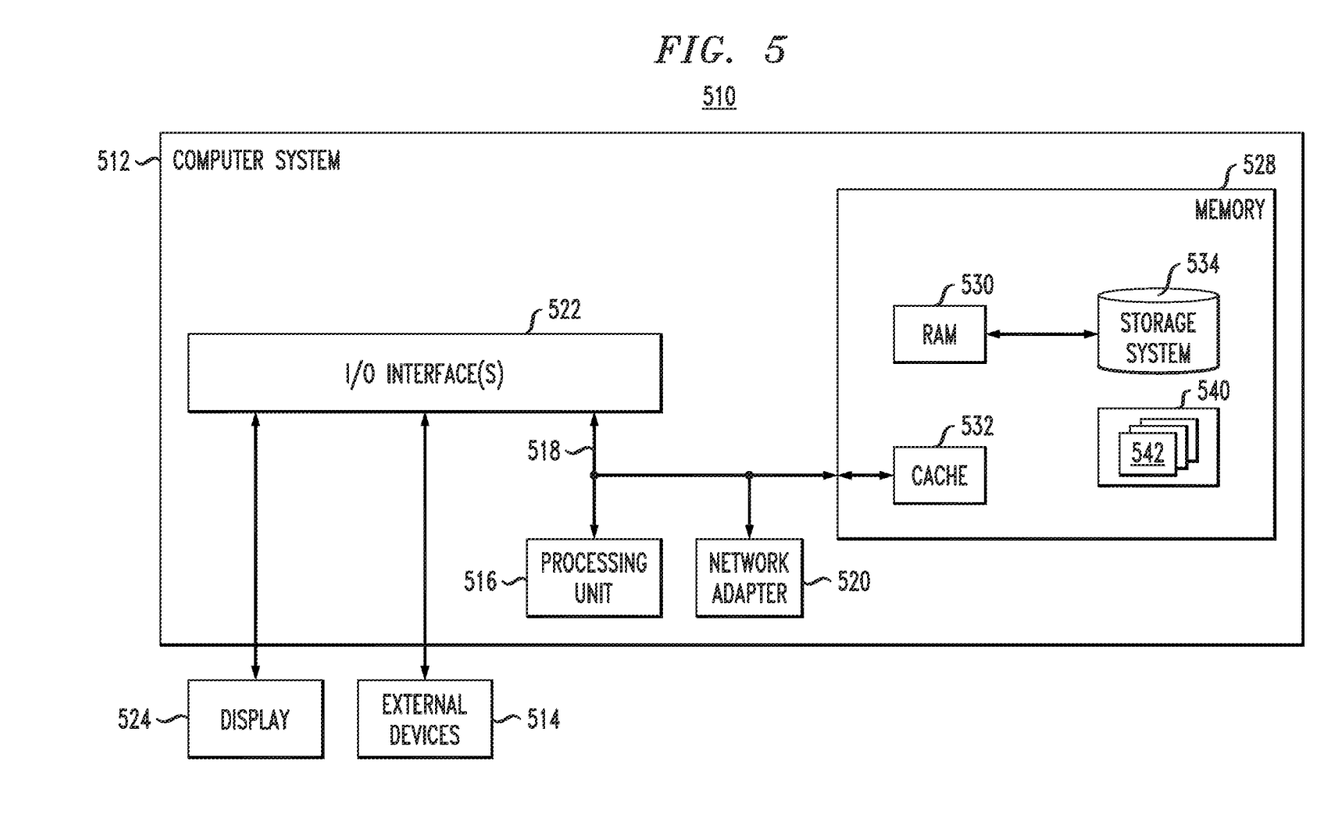
FIG. 5 depicts a computer system in accordance with which one or more components/steps of techniques of the invention may be implemented according to one or more embodiments of the invention.

One or more embodiments can make use of software running on a computer or workstation. With reference to FIG. 5, in a computing node 510 there is a system/server 512, which is operational with numerous other general purpose or special purpose computing system environments or configurations. Examples of well-known computing systems, environments, and/or configurations that may be suitable for use with system/server 512 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like. Each computing node in a computing platform can implement the architecture shown in computing node 510.

System/server 512 may be described in the general context of computer system executable instructions, such as program modules, being executed by a computer system. Generally, program modules may include routines, programs, objects, components, logic, data structures, and so on that perform particular tasks or implement particular abstract data types. System/server 512 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, system/server 512 is shown in the form of a computing device. The components of system/server 512 may include, but are not limited to, one or more processors or processing units 516, system memory 528, and bus 518 that couples various system components including system memory 528 to processor 516.

Bus 518 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

System/server 512 typically includes a variety of computer system readable media. Such media may be any available media that is accessible by system/server 512, and it includes both volatile and non-volatile media, removable and non-removable media.

The system memory 528 can include computer system readable media in the form of volatile memory, such as random-access memory (RAM) 530 and/or cache memory 532. System/server 512 may further include other removable/non-removable, volatile/nonvolatile computer system storage media. By way of example only, storage system 534 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 518 by one or more data media interfaces.

As depicted and described herein, memory 528 may include at least one program product having a set (e.g., at least one) of program modules that are configured to carry out the functions of embodiments of the invention. A program/utility 540, having a set (at least one) of program modules 542, may be stored in memory 528 by way of example, and not limitation, as well as an operating system, one or more application programs, other program modules, and program data. Each of the operating system, one or more application programs, other program modules, and program data or some combination thereof, may include an implementation of a networking environment. Program modules 542 generally carry out the functions and/or methodologies of embodiments of the invention as described herein.

System/server 512 may also communicate with one or more external devices 514 such as a keyboard, a pointing device, an external data storage device (e.g., a USB drive), display 524, one or more devices that enable a user to interact with system/server 512, and/or any devices (e.g., network card, modem, etc.) that enable system/server 512 to communicate with one or more other computing devices. Such communication can occur via I/O interfaces 522. Still yet, system/server 512 can communicate with one or more networks such as a LAN, a general WAN, and/or a public network (e.g., the Internet) via network adapter 520. As depicted, network adapter 520 communicates with the other components of system/server 512 via bus 518. It should be understood that although not shown, other hardware and/or software components could be used in conjunction with system/server 512. Examples include, but are not limited to, microcode, device drivers, redundant processing units, external disk drive arrays, RAID systems, tape drives, and data archival storage systems, etc.

Embodiments of the present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds). A cloud computing environment is service oriented with a focus on statelessness, low coupling, modularity, and semantic interoperability. At the heart of cloud computing is an infrastructure that includes a network of interconnected nodes.

Figure 6:
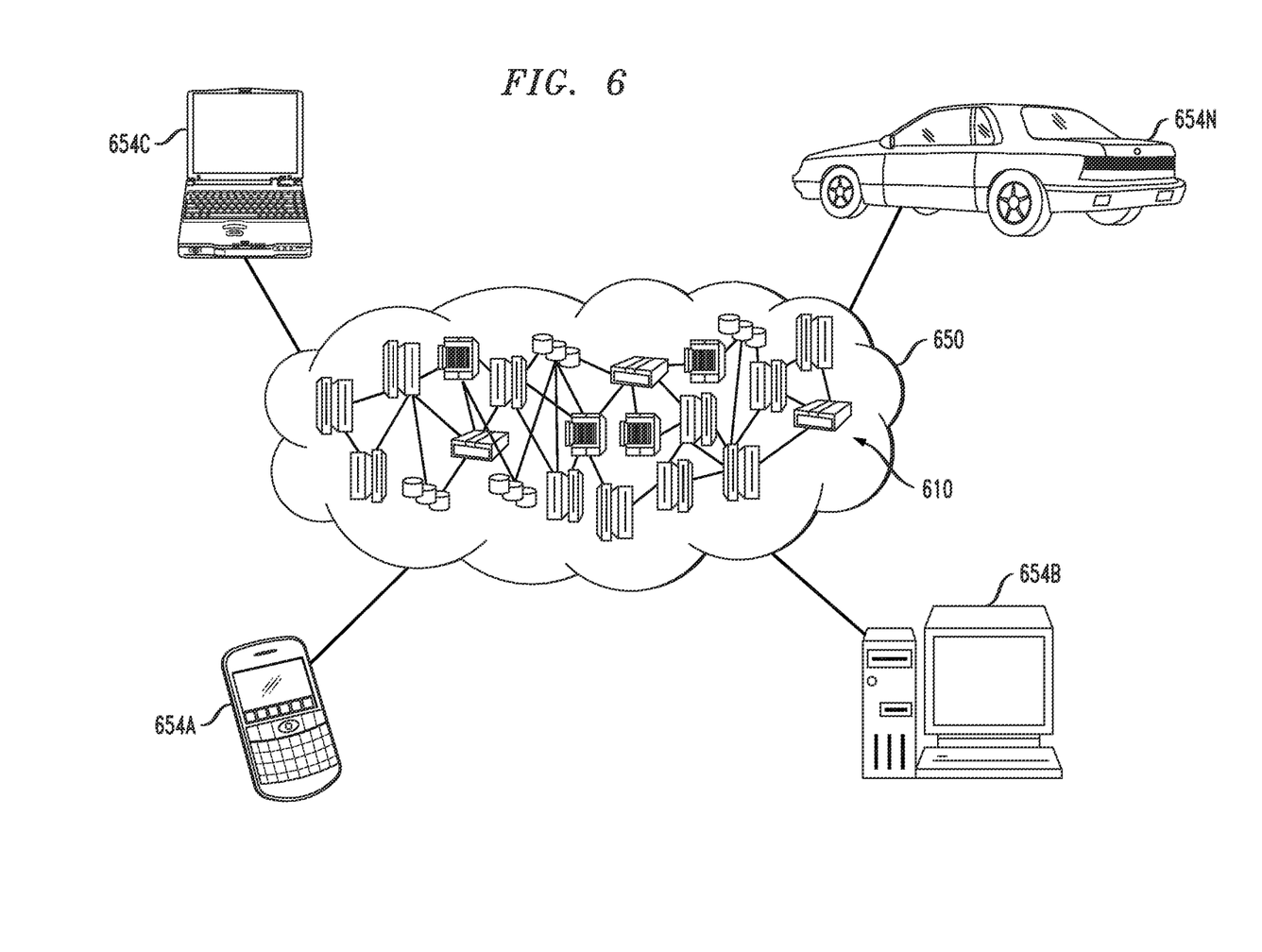
FIG. 6 depicts a cloud computing environment according to an embodiment of the invention.

Referring now to FIG. 6, illustrative cloud computing environment 650 is depicted. As shown, cloud computing environment 650 includes one or more cloud computing nodes 610 with which local computing devices used by cloud consumers, such as, for example, personal digital assistant (PDA) or cellular telephone 654A, desktop computer 654B, laptop computer 654C, and/or automobile computer system 654N may communicate. Nodes 610 may communicate with one another. They may be grouped (not shown) physically or virtually, in one or more networks, such as Private, Community, Public, or Hybrid clouds as described hereinabove, or a combination thereof. This allows cloud computing environment 650 to offer infrastructure, platforms and/or software as services for which a cloud consumer does not need to maintain resources on a local computing device. It is understood that the types of computing devices 654A-N shown in FIG. 6 are intended to be illustrative only and that computing nodes 610 and cloud computing environment 650 can communicate with any type of computerized device over any type of network and/or network addressable connection (e.g., using a web browser).

Figure 7:
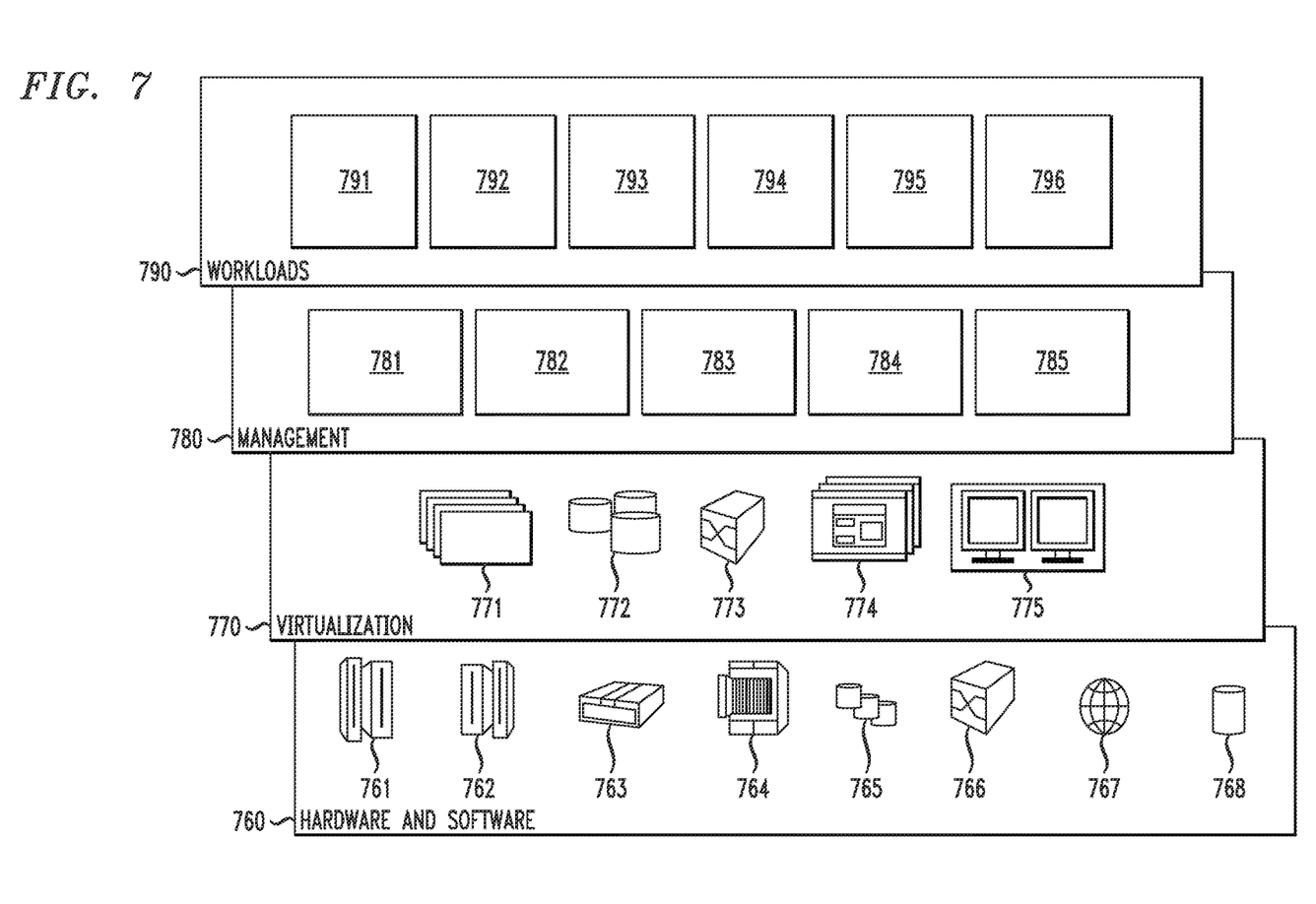
FIG. 7 depicts abstraction model layers according to an embodiment of the invention.

Referring now to FIG. 7, a set of functional abstraction layers provided by cloud computing environment 650 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 760 includes hardware and software components. Examples of hardware components include: mainframes 761; RISC (Reduced Instruction Set Computer) architecture based servers 762; servers 763;

blade servers 764; storage devices 765; and networks and networking components 766. In some embodiments, software components include network application server software 767 and database software 768.

Virtualization layer 770 provides an abstraction layer from which the following examples of virtual entities may be provided: virtual servers 771; virtual storage 772; virtual networks 773, including virtual private networks; virtual applications and operating systems 774; and virtual clients 775.

In one example, management layer 780 may provide the functions described below. Resource provisioning 781 provides dynamic procurement of computing resources and other resources that are utilized to perform tasks within the cloud computing environment. Metering and Pricing 782 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 783 provides access to the cloud computing environment for consumers and system administrators. Service level management 784 provides cloud computing resource allocation and management such that required service levels are met. Service Level Agreement (SLA) planning and fulfillment 785 provide pre-arrangement for, and procurement of, cloud computing resources for which a future requirement is anticipated in accordance with an SLA.

Workloads layer 790 provides examples of functionality for which the cloud computing environment may be utilized. Examples of workloads and functions which may be provided from this layer include: mapping and navigation 791; software development and lifecycle management 792; virtual classroom education delivery 793; data analytics processing 794; transaction processing 795; and atmospheric constituent concentration control 796.

Although illustrative embodiments have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method of controlling a gas mixture for a laser, comprising:
   receiving as an input one or more of a plurality of concentration values, wherein each of the plurality of concentration values respectively corresponds to a constituent of a plurality of constituents of air;
   generating a blend of the plurality of constituents of air based on the received one or more of the plurality of concentration values;
   determining whether the blend of the plurality of constituents of air is within a threshold range for a ratio of the plurality of concentration values for the plurality of constituents of air; and
   controlling a flow of the blend of the plurality of constituents of air to be routed through an output circuit for use as the gas mixture for the laser following a determination that the blend of the plurality of constituents of air is within the threshold range;
   wherein the method is performed by at least one computer system comprising at least one memory and at least one processor coupled to the memory.

2. The method according to claim 1, further comprising controlling a flow of the blend of the plurality of constituents of air to be routed through an exhaust system prior to determining that the blend of the plurality of constituents of air is within the threshold range.

3. The method according to claim 2, further comprising controlling a flow of the blend of the plurality of constituents of air to be transferred from a vent circuit to the output circuit following the determination that the blend of the plurality of constituents of air is within the threshold range.

4. The method according to claim 1, wherein the plurality of constituents of air comprise nitrogen, oxygen, argon and carbon dioxide ($CO_2$).

5. The method according to claim 4, wherein the threshold range corresponds to a predetermined deviation from the ratio of the plurality of concentration values for the plurality of constituents of air.

6. The method according to claim 5, wherein the ratio is about 0.04% $CO_2$, about 0.93% argon, about 20.95% oxygen and about 78.09% nitrogen.

7. The method according to claim 1, further comprising respectively monitoring a flow of one or more of the plurality of constituents of air through one or more precision devices.

8. The method according to claim 7, further comprising providing feedback from the monitoring to one or more programmable logic controllers.

9. The method according to claim 1, further comprising monitoring a flow of the blend of the plurality of constituents of air through one or more precision devices.

10. The method according to claim 9, further comprising providing feedback from the monitoring to one or more programmable logic controllers.

11. The method according to claim 1, wherein determining whether the blend of the plurality of constituents of air is within the threshold range comprises respectively monitoring a flow of one or more of the plurality of constituents of air through one or more precision devices.

12. The method according to claim 1, wherein determining whether the blend of the plurality of constituents of air is within the threshold range comprises monitoring a flow of the blend of the plurality of constituents of air through one or more precision devices.

13. The method according to claim 1, further comprising transmitting a command to close the output circuit and to control a flow of the blend of the plurality of constituents of air to be routed through an exhaust system following a determination that the blend of the plurality of constituents of air is outside of the threshold range.

14. The method according to claim 1, further comprising:
   transmitting feedback to a user regarding a size of a beam of the laser generated when using blend of the plurality of constituents of air as the gas mixture;
   providing an interface for the user to input a command to alter the one or more of the plurality of concentration values in response to the transmitted feedback; and
   generating an altered blend of the plurality of constituents of air based on the command to alter the one or more of the plurality of concentration values.

15. A system for controlling a gas mixture for a laser, comprising:
   a memory and at least one processor coupled to the memory, wherein the at least one processor is configured to:
   receive as an input one or more of a plurality of concentration values, wherein each of the plurality of concentration values respectively corresponds to a constituent of a plurality of constituents of air;

generate a blend of the plurality of constituents of air based on the received one or more of the plurality of concentration values;

determine whether the blend of the plurality of constituents of air is within a threshold range for a ratio of the plurality of concentration values for the plurality of constituents of air; and control a flow of the blend of the plurality of constituents of air to be routed through an output circuit for use as the gas mixture for the laser following a determination that the blend of the plurality of constituents of air is within the threshold range.

16. The system according to claim 15, wherein the at least one processor is further configured to control a flow of the blend of the plurality of constituents of air to be routed through an exhaust system prior to determining that the blend of the plurality of constituents of air is within the threshold range.

17. The system according to claim 16, wherein the at least one processor is further configured to control a flow of the blend of the plurality of constituents of air to be transferred from a vent circuit to the output circuit following the determination that the blend of the plurality of constituents of air is within the threshold range.

18. The system according to claim 15, wherein the plurality of constituents of air comprise nitrogen, oxygen, argon and carbon dioxide ($CO_2$), and wherein the threshold range corresponds to a predetermined deviation from the ratio of the plurality of concentration values for the plurality of constituents of air.

19. A computer program product for controlling a gas mixture for a laser, the computer program product comprising a computer readable storage medium having program instructions embodied therewith, the program instructions executable by a processor to cause the processor to perform a method comprising:

receiving as an input one or more of a plurality of concentration values, wherein each of the plurality of concentration values respectively corresponds to a constituent of a plurality of constituents of air;

generating a blend of the plurality of constituents of air based on the received one or more of the plurality of concentration values;

determining whether the blend of the plurality of constituents of air is within a threshold range for a ratio of the plurality of concentration values for the plurality of constituents of air; and controlling a flow of the blend of the plurality of constituents of air to be routed through an output circuit for use as the gas mixture for the laser following a determination that the blend of the plurality of constituents of air is within the threshold range.

20. The computer program product according to claim 19, wherein the program instructions further cause the processor to transmit a command to close the output circuit and to control a flow of the blend of the plurality of constituents of air to be routed through an exhaust system following a determination that the blend of the plurality of constituents of air is outside of the threshold range.

\* \* \* \* \*